United States Patent [19]

Nakao et al.

[11] Patent Number: 5,363,860
[45] Date of Patent: Nov. 15, 1994

[54] SUCTION TRAP AND ASSOCIATED METHOD

[76] Inventors: Naomi L. Nakao, 303 E. 57th St., New York, N.Y. 10022; Michael A. Nakao, 284 Hudson Ave., Albany, N.Y. 12210; John V. Mizzi, 30 Cramer Rd., RFD #3, Poughkeepsie, N.Y. 12603

[21] Appl. No.: 106,402

[22] Filed: Aug. 13, 1993

Related U.S. Application Data

[63] Continuation-in-part of Ser. No. 963,846, Oct. 20, 1992.

[51] Int. Cl.⁵ ............................................... A61B 5/00
[52] U.S. Cl. ..................................... 128/760; 604/319
[58] Field of Search ..................... 128/760, 768, 4, 6; 604/317, 319

[56] References Cited

U.S. PATENT DOCUMENTS

| | | | |
|---|---|---|---|
| 3,648,698 | 3/1972 | Doherty | 604/319 |
| 3,855,997 | 12/1974 | Sauer | 128/760 |
| 4,257,425 | 3/1981 | Ryan | 604/319 |
| 4,334,538 | 6/1982 | Juhn | 128/760 |
| 4,347,946 | 9/1982 | Nichols | 604/319 X |
| 4,455,140 | 6/1984 | Joslin | 604/317 |
| 4,643,197 | 2/1987 | Greene et al. | 604/319 |
| 4,813,931 | 3/1989 | Hauze | 604/319 X |
| 4,870,975 | 10/1989 | Cronk et al. | 604/317 |
| 4,957,492 | 9/1990 | McVay | 604/319 |
| 5,084,034 | 1/1992 | Zanotti | 604/319 |
| 5,197,968 | 3/1993 | Clement | 606/115 |

*Primary Examiner*—Max Hindenburg
*Attorney, Agent, or Firm*—Davis Hoxie Faithful & Hapgood

[57] ABSTRACT

A method for use in endoscopic investigations comprises the steps of providing an endoscopic insertion member with a suction line, inserting the endoscopic insertion member with the suction line into a patient, and visually inspecting organic tissues inside the patient with the endoscopic insertion member. To collect a fluid specimen, a port cover on the suction line is moved with respect to the suction line to open a port in the line. A specimen vial is coupled to the suction line at the opened port so that the suction line communicates with the vial. A vacuum is applied to the suction line to draw a fluid specimen into the vial. Subsequently, the vial is detached from the suction line, and the port cover moved back into position to again cover the port.

19 Claims, 3 Drawing Sheets

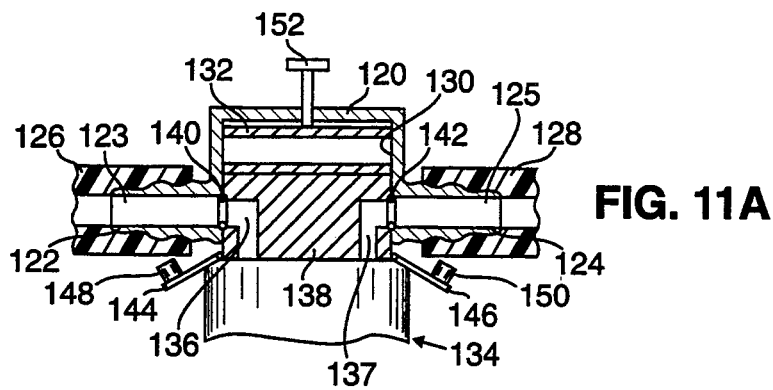
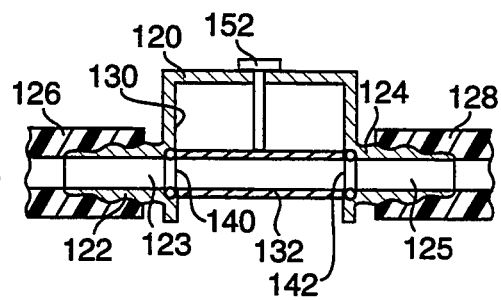
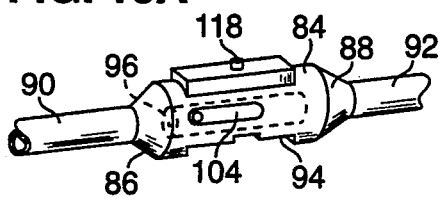
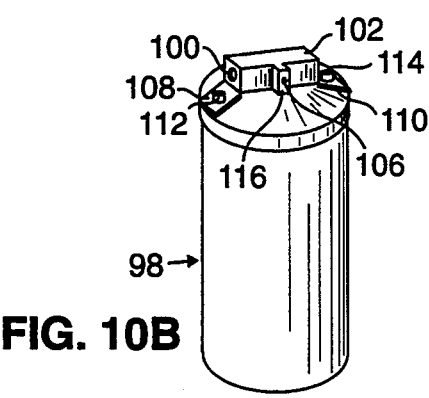
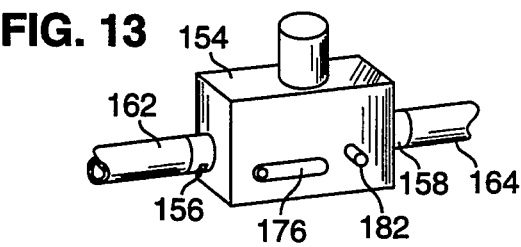
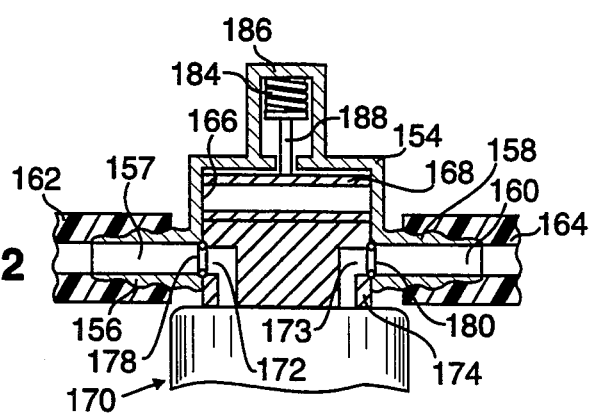

SUCTION TRAP AND ASSOCIATED METHOD

CROSS-REFERENCE TO RELATED APPLICATION

This application is a continuation-in-part of commonly owned application Ser. No. 963,846 filed Oct. 20, 1992 pending.

BACKGROUND OF THE INVENTION

This invention relates to a specimen gathering method and to an assembly utilizable in performing the method. More specifically, this invention relates to a suction trap and an associated method for use in obtaining a biological sample from a patient. The invention is particularly useful in endoscopic applications, but is not limited thereto.

In the conventional procedure for obtaining fluidic specimens during an endoscopic investigation, a vacuum line attached to the endoscope must be interrupted in its course from the endoscope. A trap is then inserted in the suction line. To implement the connection of the trap to the suction line, two short fittings are attached to the cap of a specimen trap bottle. To return the endoscope to its trapless configuration, the two fittings are detached from the vacuum line and the vacuum line is then again uninterrupted from the suction source to the endoscopic insertion member. To maintain the specimen trap bottle in an upright orientation during the specimen collection procedure, the bottle is generally held or secured to a rigid surface, for example, with adhesive tape. Upon a disconnection of the trap bottle from the suction line, the two fittings on the top of the bottle are inserted one inside the other to seal the specimen in the trap and to cover the ends of these fittings which may have some liquid contamination.

In general, a nurse or other trained person is required to assist the endoscopist during the specimen collecting procedure. Because the endoscope is inserted into the patient, the physician cannot simply abandon the scope to manipulate vacuum hoses and traps. Any simplification in the procedure that would shorten the time for attachment or detachment would be advantageous since it would reduce patient discomfort.

OBJECTS OF THE INVENTION

An object of the present invention is to provide a simplified method for attaching and detaching a specimen trap to a suction line.

Another, more particular, object of the present invention is to provide such a method which could be implemented with one hand.

Another object of the present invention is to provide a device or assembly for use in carrying out the method.

A further object of the present invention is to provide such a device or assembly which is easy to use.

Yet another object of the present invention is to provide such a device or assembly which is easy to manufacture.

These and other objects of the present invention will be apparent from the drawings and detailed descriptions herein.

SUMMARY OF THE INVENTION

A method for use in obtaining a medical or biological sample from a patient comprises, in accordance with the present invention, the steps of (a) providing a suction line, (b) inserting the suction line into a patient, (c) inserting a specimen vial into a recess in a port member provided in the suction line, (d) shifting a tubular member in the recess from a first position to a second position during the insertion of the vial, thereby disconnecting the tubular member from an inlet port and an outlet port of the port member and enabling a connection of the vial to the inlet port and the outlet port, (e) detachably locking the vial to the port member upon insertion of at least a portion of the vial into the recess, (f) applying a vacuum to the suction line to draw a fluid specimen into the vial, (g) detaching the vial from the port member upon drawing of the fluid into the vial, and (h) returning the tubular member to the first position, thereby connecting the inlet port to the outlet port via the tubular member.

According to another feature of the present invention, the step of locking includes the step of deforming a resilient member on one of the port member and the vial. The resilient member may take the form of a spring.

According to a particular feature of the present invention, the shifting of the tubular member is implemented by using the vial to push the tubular member from the first position to the second position.

The tubular member may be spring biased in the port member. In that event, the tubular member is pushed from the first position to the second position in opposition to the spring bias, while the return of the tubular member to the first position is implemented by pushing the tubular member with a spring.

In accordance with an alternative feature of the present invention, the detachment of the vial from the port member is achieved by pressing a shifting element movably mounted to the port member. The shifting element is in contact with the vial, whereby the vial is pushed out of the recess.

Where the suction line is part of an endoscope insertion member, the insertion of the vial into the recess in the port member is preferably performed subsequently to the step of inserting the endoscopic insertion member.

A suction trap assembly for use in obtaining biological (e.g., diagnostic) specimens from a patient comprises, in accordance with the present invention, a housing having an inlet opening at one end and an outlet opening at an opposite end, the inlet opening and the outlet opening being connectable to segments of a suction line which is insertable into a patient. The housing is formed with a recess between the inlet opening and the outlet opening. A tubular connector or shunt member is shiftably mounted to the housing inside the recess for motion between a first position wherein the tubular member connects the inlet opening to the outlet opening and a second position wherein the tubular member is disconnected from communicating with the inlet opening and the outlet opening. A specimen vial provided with an inlet port and an outlet port is at least partially inserted removably into the recess in the housing or port member. The tubular member is in the second, shifted, position when the vial is inserted into the recess. Cooperating elements are provided on the vial and the housing for detachably locking the vial to the housing so that the inlet port and the outlet port of the vial are juxtaposed to the inlet opening and the outlet opening of the housing when the vial is inserted into the housing, whereby the vial is in a fluid flow path extending from the inlet opening to the outlet opening of the housing.

According to another feature of the present invention, the cooperating elements includes a resilient latch member, such as a snap lock element or a spring, on the vial or the housing.

According to further features of the present invention, seals are provided on the housing for providing an essentially fluid tight seal between the housing and the vial at the inlet port and the outlet port of the vial upon insertion of the vial into the recess. Seals are also provided on the tubular member for providing an essentially fluid tight seal between the housing and the tubular member when the tubular member is in the first position.

According to an additional feature of the present invention, the suction trap assembly further comprises closure elements on the vial for sealing the inlet port and the outlet port upon a removal of the vial from the recess after the collection of a sample in the vial. The closure elements may take the form of plugs inserted into the ports on the vial.

A method in accordance with the present invention for attaching and detaching a specimen trap to an suction line (e.g., an endoscope suction line) represents a considerable simplification of the conventional procedure. The various steps in the method can be performed with one hand. The method is useful, for example, in endoscopic investigations, in the operating room or in the intensive care unit.

BRIEF DESCRIPTION OF THE DRAWING

FIG. 10A is a schematic perspective view of a port member, in accordance with the present invention, in an endoscope suction line for receiving a vial shown in FIG. 10B.

FIG. 10B is a schematic perspective view of a vial, in accordance with the present invention, received into the port member of FIG. 10A.

FIG. 11A is a schematic cross-sectional view of another port member in accordance with the present invention, similar in structure and function to the port member of FIG. 10A, with an inserted vial similar in structure and function to the vial of FIG. 10B.

FIG. 11B is a schematic cross-sectional view of the port member of FIG. 11A, with the vial removed.

FIG. 12 is a schematic cross-sectional view of yet another port member in accordance with the present invention, with a vial removably inserted into a recess in the port member.

FIG. 13 is a schematic perspective view of the port member of FIG. 12.

DETAILED DESCRIPTION

Figure 1:
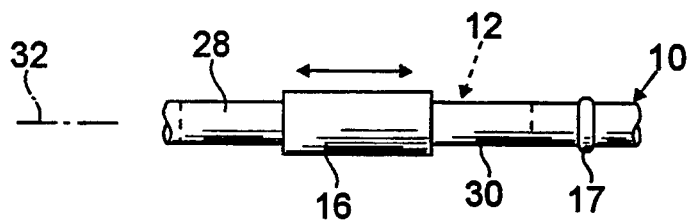
FIG. 1 is a side elevational view of a suction trap port member, on a reduced scale, in a closed configuration in an endoscope suction line.
Figure 2:
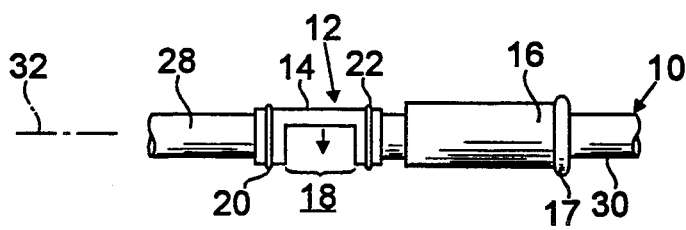
FIG. 2 is a side elevational view of the port member of FIG. 1 in an opened configuration, ready to receive a specimen container.

As illustrated in FIG. 1 and 2, a suction trap assembly for connection in a vacuum or suction line 10 of an endoscope (not shown) comprises a port member 12 including a body portion 14 and a cover sleeve 16 slidably connected to the body portion. Body portion 14 is formed with a recess 18 (FIGS. 2, 4 and 5) which is covered by sleeve 16 in a normal, closed configuration of port member 12, illustrated in FIG. 1.

At the onset of a specimen collection procedure, sleeve 16 is moved longitudinally along port member 12 until the sleeve engages a clamp 17. Clamp 17 functions as an arrest which prevents continued motion of sleeve 16.

As illustrated in FIGS. 2-5, body portion 14 of port member 12 is provided with a pair of O-rings 20 and 22 on opposite sides of recess 18. O-rings 20 and 22 are engaged by an inner surface of sleeve 16 in the closed configuration of port member 12 to seal the port member and thereby facilitate the conduction of liquid and/or gas through suction line 10.

Figure 3:
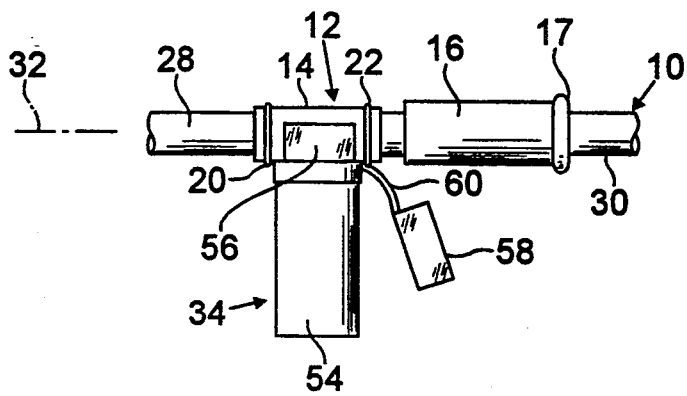
FIG. 3 is a side elevational view of the port member of FIG. 2 with an attached specimen container.
Figure 4:
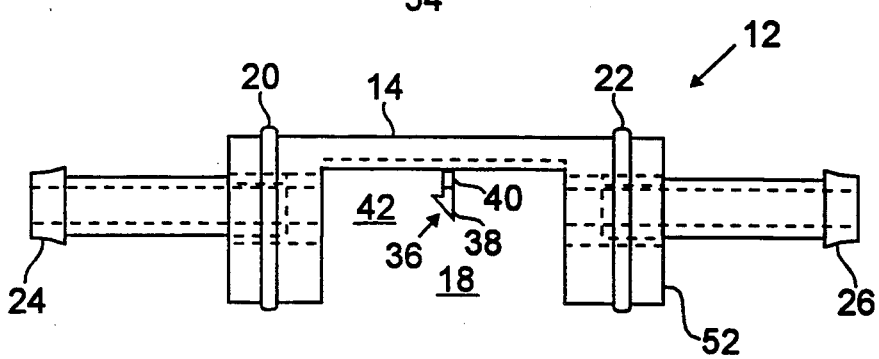
FIG. 4 is a side elevational view, on a larger scale, of a body portion of the suction trap port member of FIGS. 1-3.
Figure 5:
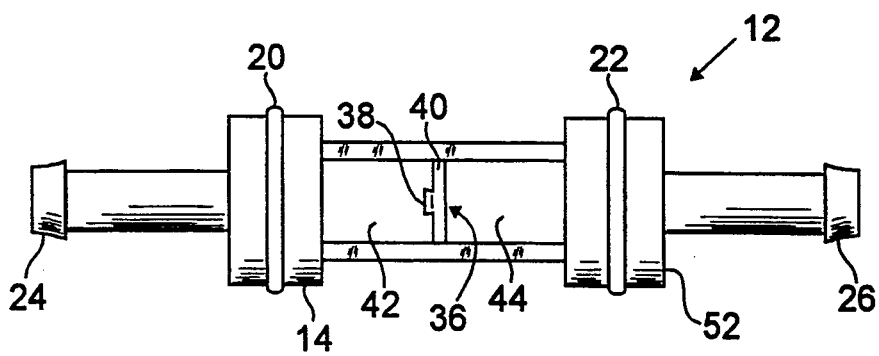
FIG. 5 is a bottom view, on a larger scale of the port member body portion of FIG. 4.

As shown in detail in FIGS. 4 and 5, body portion 14 of port member 12 is provided at opposite ends with an inlet coupling 24 and an outlet coupling 26 for connecting the port member to upstream and downstream segments 28 and 30 (FIGS. 1 and 2) of suction line 10. Inlet coupling 24 and outlet coupling 26 take the form of swivelable or rotatable ferrules which enable a rotation of port member 12 about a longitudinal axis 32 of suction line 10 upon attachment of a container member 34 (FIG. 3) to port member 12.

As shown in further detail in FIGS. 4 and 5, body portion 14 of port member 12 is provided in recess 18 with a snap lock element 36 including a hook 38 projecting from a shallow partition web 40. Partition web 40 separates an inner portion of recess 18 into two parts 42 and 44.

Figure 6:
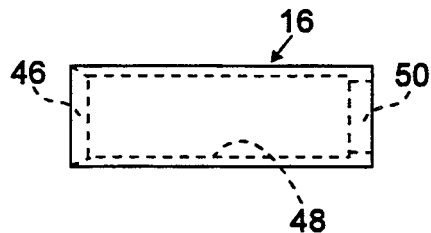
FIG. 6 is a side elevational view of a closure sleeve included in the port member of FIGS. 1-3.

As depicted in FIG. 6, sleeve 16 is a cylinder provided at one end with a beveled edge 46 for faciliating the sliding of the sleeve over O-rings 20 and 22 during a closure stroke of the sleeve over recess 18. At an opposite end, sleeve 16 is formed along an inner surface 48 with an inwardly projecting annular flange 50 for defining a closure position of sleeve 16 with respect to body portion 14 of port member 12. Flange 50 abuts against O-ring 22 or, alternatively, a shoulder 52 (FIGS. 4 and 5) of body portion 14.

Figure 7:
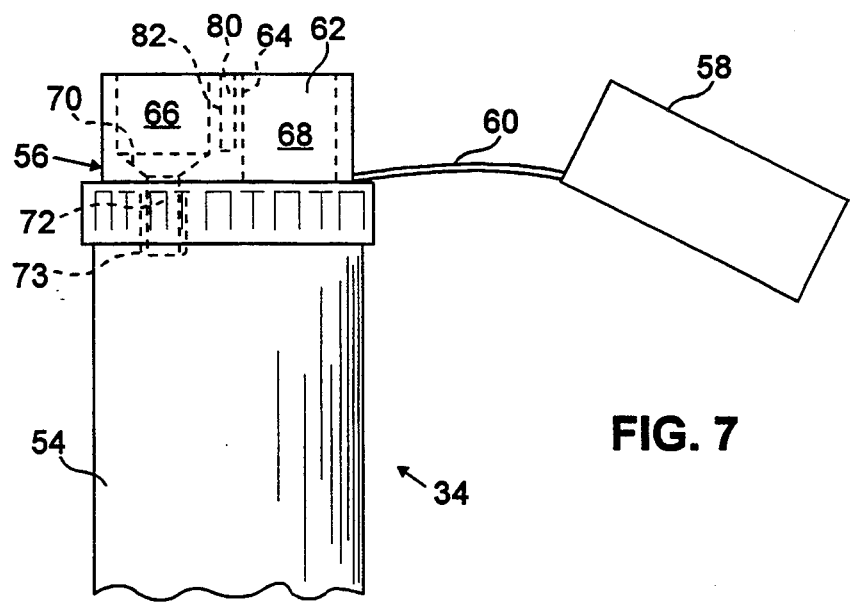
FIG. 7 is a side elevational view, on an enlarged scale, of the specimen container shown in FIG. 3.
Figure 8:
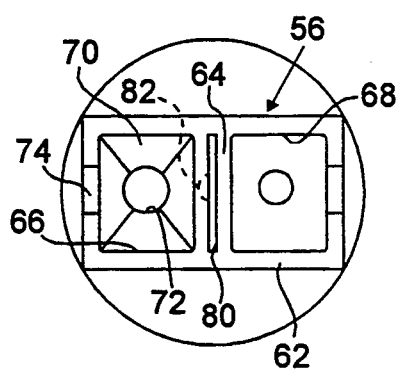
FIG. 8 is a top view of the container member of FIG. 7.
Figure 9:
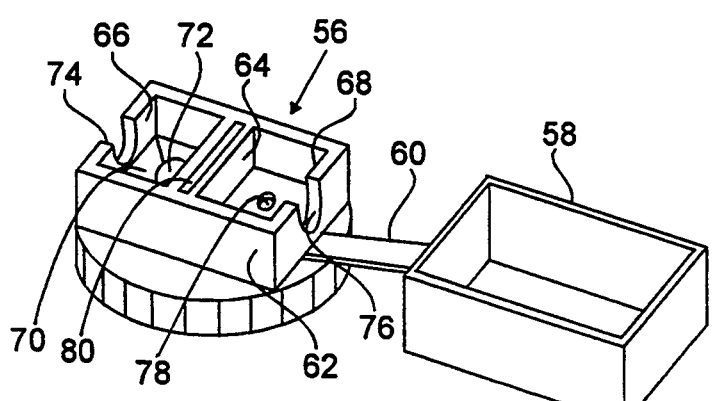
FIG. 9 is a perspective view of a head component of the container member of FIGS. 7 and 8.

As illustrated in FIGS. 3 and 7, specimen container member 34 includes a vial portion 54, a head component 56 secured to the vial, and a cap 58 movably connected to head component 56 and concomitantly to vial 54 via a flexible strap 60. As shown in FIGS. 7-9, head component 56 comprises an upwardly extending peripheral wall 62 and a partition web 64 extending between sides of wall 62 to form therewith a pair of antechambers 66 and 68. Antechamber 66 is provided in a lower region with a funnel surface 70 leading to an inlet opening 72. Funnel 70 channels incoming fluid through inlet opening 72 and a tubular extender element 73 into vial 54. The fluid enters antechamber 66 via an inlet aperture 74 formed as a slot in a side of wall 62. Antechamber 68 is also formed with such an aperture or slot 76 for enabling the evacuation of antechamber 68 via suction line segment 30 (FIGS. 1-3) and for concomitantly applying a vacuum to vial 43 during a specimen collection procedure. To that end, a lower region of antechamber 68 is provided with an outlet opening 78. Preferably, inlet opening 72 is larger than outlet opening 78.

As additionally shown in FIGS. 7-9, partition web 64 is provided with a recess or slot 80 for receiving partition web 40 on port member 12 (FIG. 4 and 5) upon an insertion of head component 56 into recess 18 during an initial stage of a specimen collection operation. At a lower end, slot 80 is provided with a transversely extending snap lock recess 82 for receiving snap lock element 36 in a snap lock fit upon insertion of head component 56 into recess 18.

Prior to the beginning of an endoscopic investigation, port member 12 is inserted into suction line 10 by connecting inlet and outlet couplings 24 and 26 to upstream and downstream suction line segments 28 and 30. Sleeve 16 is generally closed at this time. Upon subsequent insertion of an endoscopic insertion member (not shown) into a patient and upon visually inspecting internal organic tissues of the patient via optical components provided in the endoscopic insertion member, the endoscopist or an assistant slides sleeve 16 to open recess 18 and inserts head component 56 into recess 18 so that partition 40 is inserted into slot 80 of partition web 64 and so that male snap lock element 36 cooperates with female snap lock element or recess 82 to lock container member 34 to port member 12 at recess 18 (see FIG. 3). Upon attachment of container member 34 to port member 12, the port member swivels about axis 32 so that container member 34 is suspended essentially downwardly at all times. Suction is applied to line 10 so that a fluidic specimen is sucked through upstream suction line segment 28 to inlet coupling 24 and from the inlet side of port member 12 through antechamber 66 and inlet opening 72 into vial 54. A suction path continues from vial 54, through outlet opening 78 and antechamber 68 to coupling 26 and from there through downstream suction line segment 30.

Upon deposition of a specimen inside vial 54, suction may be terminated. Container member 34 is then removed from recess 18 of port member 12. The sides of body portion 14 may be squeezed to distort partition web 64 and facilitate the extraction of snap lock element 36 from snap lock recess 82.

Upon the separation of container member 34 from port member 12, cap 58 is snapped onto head component 56, thereby closing and sealing vial 54.

Sleeve 16 is moved longitudinally along body portion 14 to close recess 18 and return the suction trap assembly to the configuration disclosed in FIG. 1.

As illustrated in FIG. 10A, another suction trap assembly for use in endoscopic investigations comprises a housing or port member 84 having an inlet coupling or port 86 at one end and an outlet coupling or port 88 at an opposite end. Inlet coupling 86 and outlet coupling 88 define openings in housing 84 and are connectable to segments 90 and 92 of a suction line of an endoscope. Housing 84 is formed with a recess 94 between inlet coupling 86 and outlet coupling 88. A tubular connector or shunt member 96 is shiftably mounted to housing 84 inside recess 94 for motion in a direction substantially perpendicular to a fluid flow path extending along suction line segments 90 and 92. Tubular member 96 is shiftable between a first position wherein it is aligned with inlet coupling 86 and outlet coupling 88 (and connects the couplings) and a second position wherein the tubular member is out of alignment with and disconnected from inlet coupling 86 and outlet coupling 88.

As illustrated in FIG. 10B, a specimen vial 98 provided with an inlet port 100 and an outlet port (not illustrated) has a head portion 102 removably insertable into recess 94 in housing 84. The act of inserting head portion 102 of vial 98 into recess 94 serves to push tubular member 96 from the fluid-transmission position in alignment with couplings 86 and 88 to the neutral position laterally staggered with respect to suction line segments 86 and 88.

A resilient spring latch or detent 104 is provided on housing 84 for cooperating with a recess 106 in vial head portion 102 to detachably lock vial 98 to the housing or port member so that the inlet port 100 and the outlet port of the vial are juxtaposed to inlet coupling 86 and outlet coupling 88 of housing 84 when the vial is inserted into housing 84, whereby the vial is in a fluid flow path extending from inlet coupling 86 to outlet coupling 88 of housing 84.

Fluid-tight seals (not shown in FIGS. 10A and 10B; see FIGS. 11A, 11B, 12) are provided on housing 84 for providing an essentially fluid tight seal between housing 84 and vial 98 at the inlet port 100 and the outlet port of the vial upon insertion of the vial into recess 94. Seals may also be provided on tubular member 96 for providing an essentially fluid tight seal between housing 84 and tubular member 96 when tubular member 96 is in the aligned or fluid-transmission position.

As shown in FIG. 10B, hinged doors 108 and 110 on head portion 102 are provided with rubber closure plugs 112 and 114 for sealing the inlet port 100 and the outlet port of vial 98 upon a removal of the vial from recess 94 after the collection of a sample in the vial during an endoscopic procedure.

As further shown in FIG. 10B, head portion 102 is formed with a keying projection 116 in which recess 106 is formed. Projection 116 serves to facilitate a proper insertion of head portion 102 into recess 94.

For removing vial 98 from housing 84 upon the completion of a sample collection procedure, housing 84 is provided with an ejector button 118. Button 118 is pressed to push vial 98 out of recess 94 in opposition to the retention force exerted by spring latch 104. Pressure is exerted by button 118 on vial 98 via tubular member 96. Button 118 is in contact with tubular member 96 and may be rigidly connected thereto, although such a connection is not necessary for successful operation of the device.

As depicted in FIGS. 11A and 11B, a further suction trap assembly for use in endoscopic investigations comprises a housing or port member 120 having an inlet coupling or port 122 defining an inlet opening 123 at one end and an outlet coupling or port 124 defining an outlet opening 125 at an opposite end. Inlet coupling 122 and outlet coupling 124 are connectable to segments 126 and 128 of a suction line of an endoscope. Housing 120 is formed with a recess 130 between inlet coupling 122 and outlet coupling 124. A tubular connector or shunt member 132 is shiftably mounted to housing 120 inside recess 130 for motion in a direction substantially perpendicular to a fluid flow path extending between suction line segments 126 and 128. Tubular member 132 is shiftable between a first position wherein it is aligned with and connects inlet opening 123 and outlet opening 125 and a second position wherein the tubular member is out of alignment with and disconnected from inlet opening 123 and outlet opening 125.

As illustrated in FIG. 11A, a specimen vial 134 provided with an inlet port 136 and an outlet port 137 has a head portion 138 removably insertable into recess 130 in housing 120. The act of inserting head portion 138 of vial 134 into recess 130 serves to push tubular member 132 from the fluid-transmission position in alignment with couplings 122 and 124 to the neutral position laterally staggered with respect to suction line segments 122 and 124.

As described hereinabove with reference to FIGS. 10A and 10B, housing 120 is provided with a resilient spring latch or detent (not shown) for cooperating with a recess (not shown) in vial head portion 138 to detachably lock vial 134 to the housing or port member so that inlet port 136 and outlet port 137 of vial 134 are juxtaposed to inlet coupling 122 and outlet coupling 124 and aligned with inlet opening 123 and outlet opening 125, respectively, when the vial is inserted into housing 120, whereby the vial is in a fluid flow path extending from suction inlet segment 126 to suction outlet segment 128.

Fluid-tight seals 140 and 142 are provided on housing 120 for providing an essentially fluid tight seal between housing 120 and vial head portion 138 at inlet port 136 and outlet port 137 upon insertion of vial 134 into recess 130. Seals (not shown) may also be provided on tubular member 132 for providing an essentially fluid tight seal between housing 120 and tubular member 132 when tubular member 132 is in the aligned or fluid-transmission position.

As shown in FIG. 11A, hinged doors 144 and 146 on head portion 138 are provided with rubber closure plugs 148 and 150 for sealing inlet port 136 and outlet port 137 of vial 134 upon a removal of the vial from recess 130 after the collection of a sample in the vial during an endoscopic procedure. Head portion 138 may be formed with a keying projection (not shown), similar to keying projection 116 in FIG. 10B, in which a snap-lock closure element (such as a recess) is provided.

For removing vial 134 from housing 120 upon the completion of a sample collection procedure, housing 120 is provided with an ejector button 152. Button 152 is pressed to push vial 134 out of recess 130 in opposition to the retention force exerted by a spring latch or other resilient locking element such as a knob or ball of a ball-and-socket type snap-lock fastener. Pressure is exerted by button 152 on vial 134 via tubular member 132. Button 152 is connected to tubular member 132 but may instead be a separate element in contact with tubular member 132.

FIG. 11B illustrates housing or port member 120 with tubular member 132 in a flow-transmission position aligned with inlet and outlet openings 123 and 125 and suction line segments 126 and 128. Tubular member 132 is held in that position by friction forces, or possibly gravity in the event that swivel armatures (not shown) are provided on couplings 122 and 124 for connecting housing 120 to suction line segments 126 and 128.

Insertion of head portion 138 of vial 134 into recess 130 of housing 120 pushes tubular member 132 from the position of FIG. 11B to the position illustrated in FIG. 11A. Upon completed insertion of head portion 138 into recess 130, ports 136 and 137 are aligned with openings 123 and 125. Upon an application of suction to downstream line segment 128, fluid is sucked through upstream line segment 126, inlet opening 123, and L-shaped inlet port 136 into vial 134.

Upon completion of an endoscopic sample collection procedure, vial 134 is removed from recess 130 by pressing button 152. Tubular member 132 slides into position between inlet and outlet openings 123 and 125 during the removal of vial head portion 138 from recess 130. Upon the removal of vial 134, doors 144 and 146 are swung up so that plugs 148 and 150 are received into the outer ends of ports 136 and 137.

As depicted in FIGS. 12 and 13, yet another endoscopic suction trap assembly includes a housing or port member 154 having an inlet coupling or port 156 defining an inlet opening 157 at one end and an outlet coupling or port 158 defining an outlet opening 160 at an opposite end. Inlet coupling 156 and outlet coupling 158 are connectable to segments 162 and 164 of a suction line of an endoscope. Housing 154 is formed with a recess 166 between inlet coupling 156 and outlet coupling 158. A tubular connector or shunt member 168 is shiftably mounted to housing 154 inside recess 166 for motion in a direction substantially perpendicular to a fluid flow path extending between suction line segments 162 and 164. Tubular member 168 is shiftable between a first position wherein it is aligned with and connects inlet opening 157 and outlet opening 160 and a second position wherein the tubular member is out of alignment with and disconnected from inlet opening 157 and outlet opening 160.

As illustrated in FIG. 12, a specimen vial 170 provided with an inlet port 172 and an outlet port 173 has a head portion 174 removably insertable into recess 166 in housing 154. The act of inserting head portion 174 of vial 170 into recess 166 serves to push tubular member 168 from the fluid-transmission position in alignment with couplings 156 and 158 to the neutral position laterally staggered with respect to suction line segments 162 and 16417.

As depicted in FIG. 13, housing 154 is provided with a resilient spring latch or detent 176 for cooperating with a recess (not shown) in vial head portion 174 to detachably lock vial 170 to housing or port member 154 so that inlet port 172 and outlet port 173 of vial 170 are juxtaposed to and aligned with inlet coupling 156 and outlet coupling 158, respectively, when the vial is inserted into housing 154, whereby the vial is in a fluid flow path extending from suction inlet segment 162 to suction outlet segment 164.

Fluid-tight seals 178 and 180 are provided on housing 154 for providing an essentially fluid tight seal between housing 154 and vial head portion 174 at inlet port 172 and outlet port 173 upon insertion of vial 170 into recess 166.

Hinged doors with rubber closure plugs (not illustrated) may be provided on head portion 174 for sealing the inlet port 172 and outlet port 173 of vial 170 upon a removal of the vial from recess 166 after the collection of a sample in the vial during an endoscopic procedure. Head portion 174 may be formed with a keying projection (not shown), similar to keying projection 116 in FIG. 10B, in which a snap-lock closure element (such as a recess) is provided.

For removing vial 170 from housing 154 upon the completion of a sample collection procedure, housing 154 is provided with an ejector button 182. Button 182 is pressed to release spring latch 176 from vial 170 and thereby enable the ejection of vial 170 by a compression spring 184 disposed in an extension 186 of housing 154.

Insertion of head portion 174 of vial 170 into recess 166 of housing 154 pushes tubular member 168 from a fluid-transmission position to a transversely shifted position (FIG. 12) in opposition to the return force exerted by compression spring 184. Upon completed insertion of head portion 174 into recess 166, ports 172 and 173 are aligned with openings 157 and 160. Upon an application of suction to downstream line segment 164, fluid is sucked through upstream line segment 162, inlet opening 156, and L-shaped inlet port 172 into vial 170.

Upon completion of an endoscopic sample collection procedure, vial 170 is removed from recess 166 by pressing button 182. Compression spring 184 acts via a pusher element 188 to slide tubular member 168 into position between inlet and outlet openings 157 and 160 during the removal of vial head portion 174 from recess 166.

Although the invention has been described in terms of particular embodiments and applications, one of ordinary skill in the art, in light of this teaching, can generate additional embodiments and modifications without departing from the spirit of or exceeding the scope of the claimed invention. The locking of a vial to a suction trap port member may be accomplished in any number of equivalent ways. For example, resilient ball-and-socket fasteners may be used instead of leaf springs 104 and 176; a quarter-turn threaded twist collar can also be used for this purpose. Inlet ports 100, 136, 172 and outlet ports 137 and 173 may be closed alternatively by caps or plugs, sliding doors or hinged doors, etc. Spring 184 may be located inside housing 154 itself.

Accordingly, it is to be understood that the drawings and descriptions herein are proffered by way of example to facilitate comprehension of the invention and should not be construed to limit the scope thereof.

What is claimed is:

1. A method for use in obtaining medical specimens, comprising the steps of:
   providing a suction line, said suction line being provided with a port member having a recess and a shiftable tubular member mounted to said port member in said recess, said port member also having an inlet port and an outlet port communicating with said recess;
   inserting said suction line into a patient;
   inserting a specimen vial into said recess in said port member;
   during said step of inserting said vial, shifting said tubular member in said recess from a first position to a second position, thereby disconnecting said tubular member from said inlet port and said outlet port and enabling a connection of said vial to said inlet port and said outlet port;
   detachably locking said vial to said port member upon insertion of at least a portion of said vial into said recess;
   applying a vacuum to said suction line to draw a fluid specimen into said vial;
   upon drawing of said fluid into said vial, detaching said vial from said port member; and
   returning said tubular member to said first position, thereby connecting said inlet port to said outlet port via said tubular member.

2. The method defined in claim 1 wherein said step of locking includes the step of deforming a resilient member on one of said port member and said vial.

3. The method defined in claim 2 wherein said resilient member is a spring.

4. The method defined in claim 1 wherein said step of shifting said tubular member includes the step of using said vial to push said tubular member from said first position to said second position.

5. The method defined in claim 4 wherein said tubular member is spring biased in said port member, said tubular member being pushed from said first position to said second position in opposition to the spring bias, said step of returning including the step of pushing said tubular member with a spring.

6. The method defined in claim 1, further comprising the step of providing an endoscopic insertion member, said suction line being connected to said insertion member, said step of inserting said suction line into the patient including the step of inserting said insertion member into the patient, also comprising the step of visually inspecting organic tissues inside said patient with said endoscopic insertion member;

7. The method defined in claim 6, further comprising the step of withdrawing said endoscopic insertion member from the patient, said steps of detaching and returning being performed prior to said step of withdrawing.

8. The method defined in claim 6 wherein said step of inserting said vial is performed subsequently to said step of inserting said endoscopic insertion member.

9. The method defined in claim 1 wherein said step of returning includes the step of pushing said tubular member with a spring.

10. The method defined in claim 1 wherein said step of detaching includes the step of pressing a shifting element movably mounted to said port member, said shifting element contacting said vial, whereby said vial is pushed out of said recess.

11. The method defined in claim 1, further comprising the step of rotating said vial with respect to said suction line after said step of locking.

12. A suction trap assembly for use in obtaining biological specimens from patients, comprising:
   a housing having an inlet opening at one end and an outlet opening at an opposite end, said inlet opening and said outlet opening being connectable to segments of a suction line, said housing being formed with a recess between said inlet opening and said outlet opening;
   a tubular member shiftably mounted to said housing inside said recess for motion between a first position wherein said tubular member connects said inlet opening to said outlet opening and a second position wherein said tubular member is disconnected from communicating with said inlet opening and said outlet opening;
   a specimen vial provided with an inlet port and an outlet port, at least a portion of said vial being removably inserted into said recess, said tubular member being in said second position when said portion of said vial is inserted into said recess; and
   cooperating means on said vial and said housing for detachably locking said vial to said housing so that said inlet port and said outlet port are juxtaposed to said inlet opening and said outlet opening when said portion of said vial is inserted into said housing, whereby said vial is in a fluid flow path extending from said inlet opening to said outlet opening of said housing.

13. The assembly defined in claim 12 wherein said cooperating means includes a resilient latch member on one of said vial and said housing.

14. The assembly defined in claim 13 wherein said resilient latch member is a spring.

15. The assembly defined in claim 12, further comprising sealing means on said housing for providing an essentially fluid tight seal between said housing and said vial at said inlet port and said outlet port upon insertion of said vial into said recess.

16. The assembly defined in claim 12, further comprising sealing means on said housing and said tubular member for providing an essentially fluid tight seal between said housing and said tubular member while said tubular member is in said first position.

17. The assembly defined in claim 12, further comprising closure means on said vial for sealing said inlet port and said outlet port upon a removal of said vial from said recess after the collection of a sample in said vial during an endoscopic procedure.

18. The assembly defined in claim 12 wherein said inlet coupling and said outlet coupling include means for enabling a rotation of said port member relative to said suction line.

19. The assembly defined in claim 12, further comprising means for ejecting said vial from said recess upon a collection of a sample in said vial during an endoscopic procedure.

* * * * *